United States Patent
Pascoe

(10) Patent No.: US 6,426,076 B1
(45) Date of Patent: Jul. 30, 2002

(54) ASCORBIC ACID AS AN ADJUVANT IN THE TREATMENT OF MALIGNANT TUMORS USING CHEMOTHERAPY AND RADIOTHERAPY

(75) Inventor: Jürgen F. Pascoe, Pohlheim (DE)

(73) Assignee: PASCO Pharmazeutische Präparate GmbH, Giessen (DE)

( * ) Notice: Subject to any disclaimer, the term of this patent is extended or adjusted under 35 U.S.C. 154(b) by 0 days.

(21) Appl. No.: 09/381,088

(22) PCT Filed: Jan. 30, 1998

(86) PCT No.: PCT/EP98/00487

§ 371 (c)(1),
(2), (4) Date: Dec. 15, 1999

(87) PCT Pub. No.: WO98/41204

PCT Pub. Date: Sep. 24, 1998

(30) Foreign Application Priority Data

Mar. 15, 1997 (DE) .......................................... 197 10 907

(51) Int. Cl.[7] .............................. A61K 9/00; A61K 31/34
(52) U.S. Cl. ........................................ 424/400; 514/474
(58) Field of Search .............................. 424/401, 400; 514/395, 474

(56) References Cited

U.S. PATENT DOCUMENTS 5,900,429 A * 5/1999 Camden ...................... 514/395

OTHER PUBLICATIONS

Riordan, H.D., et al., "Case Study: High–Dose Intravenous Vitamin C in the Treatment of a Patient with Adenocarcinoma of the Kidney", Journal of Orthomolecular Medicine, vol. 5, No. 1, 1990, pp. 5–7.
Lyn–Cook, L.E., et al., "Vitamin C Intake Influences Cell Proliferation and Mutagenicity Induced by Benzo(a)Pyrene(BP) and Bleomycin(BM) in the Rat", Environ. Mol. Mutagen., vol. 25, No. 525, 1995, p. 32.
Tewfik, F.A., et al., "The Influence of Ascorbic Acid on Growth of Solid Tumors in Mice and on Tumor Control by X–Irradiation", Int. J. Vitam. Nutr. Res. Suppl., vol. 23, 1982, pp. 257–263.
Clemens, M.R., "Vitamine und Therapie von Malignomen", Therapeutische Umschau, Band 51, 1994, Heft 7, pp. 483–488.

Taper, H.K.S., "Potentiation of Radiotherapy by Nontoxic Pretreatment with Combined Vitamins C and K$_3$ in Mice Bearing Solid Transplantable Tumor", Anticancer Research 16, 1996, pp. 499–504.
Dorr, R.T., "Bleomycin Compatibility with Selected Intravenous Medications", Journal of Medicine, vol. 13, Nos. 1 and 2, 1982, pp. 121–130.
Clemens, M.R., et al., "Vitamine bei hochdosierter Chemo und Strahlentherapie", Z Ernährungswiss 31, 1992, pp. 110–120.
Narra, V.R., et al., "Vitamin C as a Radioprotector Against Iodine–131 In Vivo", The Journal of Nuclear Medicine, vol. 34, No. 4, Apr. 1993, pp. 637–640.
Rivas–Olmedo, G., et al., Inhibition of mitomycin C–induced sister chromatid exchanges by vitamin C in vivo.
Bickers, D.R., et al., "Enhancement of bleomycin–mediated DNA damage by epidermal microsomal enzymes".
Cameron, E., et al., "Supplemental ascorbate in the supportive treatment of cancer: Reevaluation of prolongation of survival times in terminal human cancer", Proc. Natl. Acad. Sci. USA 75, 1978, pp. 4538–4542.
Campbell et al., "Reticulum Cell Sarcoma:Two Complete 'Spontaeous' Regressions, in response to High–Dose Ascorbic Acid Therapy", Oncology, vol. 48, 1991, pp. 495–497.*
Cameron "Protocol for use of Vitamin C in the Treatment of Cancer", Medical Hypotheses, vol. 36, 1991, pp. 190–196.*
Taper et al., "Potentiation of Radiotherapy by Nontoxic Pretreatment with combined Vitamins C and K3 in Mice Bearing Solid Transplantable Tumor", Anticancer Research 16, 1996, pp. 499–504.*

* cited by examiner

Primary Examiner—Thurman K. Page
Assistant Examiner—Blessing Fubara
(74) Attorney, Agent, or Firm—Collard & Roe, P.C.

(57) ABSTRACT

The use of ascorbic acid or one of its salts for the production of a pharmaceutical drug suitable for parenteral administration that contains more than 5 g of ascorbic acid or one of its salts and is used as an adjuvant in the chemotherapy and radiotherapy of tumors is described. Reference is also made to a combination preparation that has, in a separate packaging unit, (a) a ready-to-use pharmaceutical preparation suitable for parenteral administration containing ascorbic acid or one of its salts, and (b) a ready-to-use pharmaceutical preparation suitable for parenteral administration containing a chemotherapeutically active cytostatic agent, which are used for concomitant or separate or preferably staggered administration in the chemotherapy or radiotherapy of tumors.

14 Claims, No Drawings

ASCORBIC ACID AS AN ADJUVANT IN THE TREATMENT OF MALIGNANT TUMORS USING CHEMOTHERAPY AND RADIOTHERAPY

This application is a U.S. National Stage Application of PCT Application No. PCT/EP98/00487, which is herein incorporated by reference.

BACKGROUND OF THE INVENTION

1. Field of the Invention

The present invention relates to the use of ascorbic acid in combination with chemotherapeutic drugs to increase the inhibitory effects of the chemotherapy and to reduce its serious side effects and the use of ascorbic acid for radioprotection in radiotherapy.

2. The Prior Art

It is known that some types of cancer, such as lymphoblastic anemia, Hodgkin's disease and testicular tumors respond very well to chemotherapy, which is constantly being improved. However, there are many types of cancer, some of them very widespread, which do not respond adequately to chemotherapy. Administration of chemotherapeutic agents is often associated with substantial side effects, such as loss of hair, nausea, vomiting, cardiomyopathy, bone marrow suppression, immunosuppression, hematopoietic dysfunction, leukopenia, etc. Therefore, there is a great demand for pharmaceutical drugs that increase the susceptibility of cancer cells to chemotherapeutic agents as well as drugs that mitigate or completely suppress the side effects observed with the use of chemotherapeutic agents as well as radiation therapy.

In addition, it is known from epidemiological studies that there is a close correlation between the vitamin C status and the incidence of certain types of tumors. Low plasma levels of vitamin C correlate closely with the risk of developing cancer of the esophagus, larynx, oral cavity, pancreas, stomach, rectum, breast and cervix. By reducing carcinogenic and mutagenic substances in the body, vitamin C has an important protective function. The preventive effect of vitamin C with respect to tumors of the gastrointestinal tract can be explained in part by the ability of the vitamin to prevent the formation of nitrosamines. It is also known that vitamin C is one of the most effective antioxidants in the human body. Free radicals are formed by endogenous metabolites and are induced by exogenous substances or radiation. Free radicals can damage proteins, enzymes, lipids and the genetic material. Studies on human blood plasma have shown that vitamin C is especially effective as protection against peroxy radicals. Water-soluble vitamin C regenerates (chemically reduces) oxidized vitamin E and thus provides additional protection for the lipid membranes.

One of the first studies of the use of vitamin C in cancer therapy was conducted by Cameron and Pauling. The group of volunteers included 100 terminal cancer patients who received 10 g of vitamin C orally each day. The control group consisted of 1000 patients receiving a comparable therapy without vitamin C. The survival time of the cancer patients treated with vitamin C was longer than that of the control group. E. Cameron, L. Pauling, *Proc. Natl. Acad. Sci. USA* 75, 4538–42 (1978).

In addition, Cameron has described a therapeutic concept for treatment of cancer patients based on adjuvant, high-dose intravenous vitamin C therapy (0.5 to 10 g/day), followed by continuous oral doses of vitamin C (10 to 30 g). E. Cameron. *Medical Hypotheses* 36,190–194 (1991). The following effects of this therapy were described:

1. improvement in general well-being and the Karnofsky scale,
2. relief from pain in cases of skeletal metastasis,
3. decline in protein tumor markers in the serum,
4. in favorable cases, absorption of malignant pleural effusions and a reduction in the size of pulmonary metastases.

E. Cameron; *Medical Hypotheses* 36, 190–194 (1991)

In addition, there are examples of cases in the literature where an improvement in general condition and spontaneous remissions have been described in conjunction with high-dose vitamin C therapy in cancer patients. H. D. Riordan J. A. Jackson, M. J. Schultz. *Orthomolecular Med.* 5 (1), 5–7 (1990); A. Campbell, T. Jack, E. Cameron. *Oncology* 48 (6) 495–497 (1991).

The positive findings by Cameron and Pauling E. Cameron, L. Pauling, *Proc. Natl. Acad Sci. USA* 75, 4538–42 (1978) were not confirmed subsequently in some cases, but in vitro tests on cell lines have indicated that vitamin C in certain concentrations has a cytotoxic effect on tumor cell lines. However, findings obtained on cell cultures cannot readily be applied to in vivo conditions. Nevertheless, it can be regarded as confirmed that vitamin C in certain concentrations has a cytotoxic effect on tumor cell lines. The growth of normal cell lines is therefore not influenced in these concentrations. Thus, vitamin C has a differentiated effect on the growth of neoplastic cell lines and normal cell lines. Whether vitamin C is a therapeutic agent with a cytotoxic effect on tumor cells cannot yet be decided on the basis of research results available so far.

More important than the cytotoxic potential of vitamin C on tumor cells is the effect of this vitamin on the entire body which has been weakened by the cancer process. Vitamin C increases the body's defense mechanisms in various ways. This affects both the cellular and humoral immune response of the body. Vitamin C stimulates lymphocytic blastogenesis and promotes the mobility and chemotaxis of neutrophils, eosinophils and monocytes, and leads to definite improvement in the blood picture by stabilizing platelet count and white blood cell count despite concomitant chemotherapy. In the area of the humoral immune response, high doses of vitamin C lead to increased antibody production and stimulate phagocytosis.

Vitamin C even increases the immune response in the presence of carcinogens such as dibutylamine and sodium nitrite as substance that produce nitrosamines, which normally lead to suppression of the cellular and humoral immune response. In addition to strengthening the immune system, vitamin C is also indispensable for the integrity of the membrane and the stability of the connective tissue. In addition, pain is diminished, especially in cases of skeletal metastasis, and side effects such as nausea and vomiting are reduced.

It has already been observed that enteral nutrition is often disturbed with regard to quantity and absorption during chemotherapy and radiation therapy. This applies in particular to the antioxidant vitamins alpha-tocopherol, beta-carotene and ascorbic acid. At the same time, however, the intracellular antioxidant potential is often reduced by cytostatics. It can be assumed that the cytotoxic effect of the anthracyclines, mitomycin and etoposide, in particular, is attributable in large part to the formation of aggressive radicals. The consequences of these oxidative processes induced by chemotherapeutic drugs are damage to membranes, proteins, enzymes and genetic material.

To determine whether antioxidant vitamin supplements can compensate for this loss, a study has already been conducted on 22 patients. These patients received daily oral doses of 825 mg DL-alpha-tocopherol, 45 mg beta-carotene and 450 mg ascorbic acid three weeks before the start of chemotherapy and radiation therapy. In addition to definitely reduced lipid peroxide concentrations in the blood, signs of reduced hepatotoxicity of the chemotherapy were observed in the patients receiving such supplements M. R. Clemens. *Therapeutiische Rundschau*, Volume 51, 483–488, 1994. However, it has been impossible to determine from this the influence of orally administered antioxidant vitamins on the antineoplastic effect of chemotherapy and radiation therapy and whether the side effects thereof are reduced in this way. Since absorption after oral administration may also be impaired during chemotherapy and radiation therapy, these experiments do not permit any conclusions regarding the effects of parenteral administration of high doses of vitamin C preparations over a period of several weeks.

SUMMARY OF THE INVENTION

It has now been discovered that ascorbic acid or its physiologically acceptable salts greatly improve the success of chemotherapy and radiation therapy while reducing their side effects when administered parenterally in a dose of more than 5 g as an adjuvant to chemotherapy or radiation therapy. In general, ascorbic acid or its salts are used in an amount of 5.0 to 30.0 g, preferably in an amount of 5.0 to 10.0 g. The parenteral preparation should have a pH between 6.0 and 8.0. As a result, an increase in the inhibitory effects of the chemotherapeutic drug and a tissue-protective effect in radiation therapy as well as a reduction in the sometimes very serious side effects have been observed. This surprising synergism occurs in vitro with a combination of a vitamin C therapy with such chemotherapeutic drugs as adriamycin, bleomycin sulfate, mitomycin C, methotrexate, vincristine sulfate, 5-fluorouracil, paclitaxel, doxorubicin and cisplatin. In animal experiments, a prolonged survival time was demonstrated with the combination with adriamycin.

DETAILED DESCRIPTION OF PREFERRED EMBODIMENTS

The combination preparation contains, in a separate packing unit,
a) a ready-to-use pharmaceutical preparation suitable for parenteral administration, containing ascorbic acid or one of its salts, and
b) a ready-to-use pharmaceutical preparation suitable for parenteral administration, containing a chemotherapeutically active cytostatic agent,
which is used for concomitant or separate or preferably staggered administration in chemotherapy or radiation therapy of tumors.

The effects of ascorbic acid as an adjuvant in tumor therapy are emphasized by the following case examples.

Case 1

In a female patient with a mastectomy of the right breast because of a carcinoma and subsequent multiple local recurrences and skin metastases, vitamin C infusions of 7.5 g per infusion were administered. The vitamin C infusions led to a remission of the skin metastases. The vitamin C therapy was superior to the local-acting cytostatic administered previously.

Case 2

Ten infusions of 7.5 g vitamin C each were administered to a female patient with metastatic breast cancer and massive bone metastases. There was a definite improvement in the blood picture (stabilization of leukocytes and platelets) despite concomitant chemotherapy. The vitamin C therapy brought great relief from the pain caused by the bone metastases.

It is noteworthy that the effects of the cytostatics tested are not impaired by the administration of large amounts of ascorbic acid or its salts. It is considered confirmed today that many cytotoxic drugs have a cytotoxic effect on tumor tissue by a mechanism of generating free radicals. The side effects of chemotherapy are also attributed to an increase in the levels of free radicals in many tissues. Theoretically, adjuvant administration of antioxidants such as ascorbic acid or its salts would have to lead to a reduction in free radical concentrations and thus to a diminished effect of the chemotherapeutic drugs. However, the findings available to date do not indicate any such interactions. In combination therapy with vitamin C, no loss of effect was observed with any of the cytostatics investigated. However, to reduce the loss of effect in chemotherapy, which theoretically cannot be ruled out entirely, it is advisable not to administer ascorbic acid simultaneously and together with the chemotherapeutic drug, but instead to administer ascorbic acid in the intermissions in chemotherapy to restore the vitamin C level depressed by the disease and the chemotherapy. Preferably an interval of at least 24 hours should be observed between administration of the chemotherapeutic drug and vitamin C.

It has also been found that adjuvant vitamin C injections increase the radiation tolerance of normal tissue (skin and bone marrow) without at the same time necessitating a change in the radiation dose required to decrease the tumorous tissue. An intravenous infusion of 7.5 g of vitamin C before and after each radiation yields clearly positive results. Skin reactions accompanying radiation can be prevented, and the radioprotective effect on bone marrow greatly improved by vitamin C. With vitamin C infusions, the radiation tolerance of normal tissue is raised by about 20% without increasing the radiation dose required to remove the tumors. This is also a sign that vitamin C has a differentiated effect on normal tissue and tumorous tissue.

What is claimed is:

1. A method for the treatment of malignant tumors, consisting of:
parenteral administration to a patient of vitamin C in staggered administration in dosage amounts greater than about 5 g that are effective as an adjuvant in chemotherapy or radiotherapy; and
said parenteral administration of vitamin C occurring in an interval of at least 24 hours before or after radiation therapy or chemotherapy.

2. The method according to claim 1, wherein the vitamin C is selected from the group consisting of ascorbic acid and its pharmacologically acceptable salts.

3. The method according to claim 1, wherein the pharmaceutical drug has a pH between about 6 and about 8.

4. The method according to claim 1, wherein the dosage amount is greater than about 5.0 g to about 30.0 g.

5. The method according to claim 1, wherein the dosage amount is greater than about 5.0 g to about 10.0 g.

6. The method according to claim 4, wherein the dosage amount is administered before a radiotherapy treatment.

7. The method according to claim 5, wherein the dosage amount is administered before a radiotherapy treatment.

8. The method according to claim 4, wherein the dosage amount is administered after a chemotherapy treatment.

9. The method according to claim 5, wherein the dosage amount is administered after a chemotherapy treatment.

10. A combination product, in a single packaging unit consisting of:

a) a ready-to-use pharmaceutical preparation suitable for parenteral administration, containing vitamin C as sole pharmaceutical effective component; and b) a ready-to-use pharmaceutical preparation suitable for parenteral administration, containing a chemotherapeutically active cytostatic agent, as sole pharmaceutical effective component, which are used for staggered administration in chemotherapy or radiation therapy of tumors; and said parenteral administration of vitamin C occurring in an interval of at least 24 hours before or after radiation therapy or chemotherapy.

11. The combination product according to claim 10, wherein the vitamin C is selected from the group consisting of ascorbic acid and its pharmacologically acceptable salts.

12. The combination product according to claim 10, wherein the chemotherapeutically active cytostatic agent comprises: adriamycin, bleomycin sulfate, mitomycin C, methotrexate, vincristine sulfate, 5-fluorouracil, paclitaxel, doxorubicin or cisplatin as the chemotherapeutically active cytostatic agent.

13. The method according to claim 8, wherein the chemotherapeutic treatment employs adriamycin, bleomycin sulfate, mitomycin C, methotrexate, vincristine sulfate, 5-fluorouracil, paclitaxel, doxorubicin or cisplatin as the chemotherapeutically active cytostatic agent.

14. The method according to claim 9, wherein the chemotherapeutic treatment employs adriamycin, bleomycin sulfate, mitomycin C, methotrexate, vincristine sulfate, 5-fluorouracil, paclitaxel, doxorubicin or cisplatin as the chemotherapeutically active cytostatic agent.

* * * * *